United States Patent
Meneghetti et al.

(10) Patent No.: US 7,445,797 B2
(45) Date of Patent: Nov. 4, 2008

(54) ENHANCED BORON NITRIDE COMPOSITION AND POLYMER-BASED COMPOSITIONS MADE THEREWITH

(75) Inventors: Paulo Meneghetti, Avon, OH (US); Paul Joseph Hans, Medina, OH (US); Gregory W. Shaffer, Strongsville, OH (US)

(73) Assignee: Momentive Performance Materials Inc., Albany, NY (US)

( * ) Notice: Subject to any disclaimer, the term of this patent is extended or adjusted under 35 U.S.C. 154(b) by 0 days.

(21) Appl. No.: 11/248,095

(22) Filed: Oct. 12, 2005

(65) Prior Publication Data

US 2007/0041918 A1 Feb. 22, 2007

Related U.S. Application Data

(60) Provisional application No. 60/661,395, filed on Mar. 14, 2005.

(51) Int. Cl.
*A61K 9/14* (2006.01)
*A61K 9/16* (2006.01)
*A61K 33/32* (2006.01)
*A01N 59/14* (2006.01)
*C08G 63/698* (2006.01)

(52) U.S. Cl. .................. 424/490; 424/489; 424/657; 424/718; 525/10; 525/11; 525/12

(58) Field of Classification Search ................ 424/489, 424/490, 657, 682, 718; 525/10, 11, 12
See application file for complete search history.

(56) References Cited

U.S. PATENT DOCUMENTS

| 4,623,738 A | 11/1986 | Sugerman et al. |
|---|---|---|
| 4,634,785 A | 1/1987 | Sugerman et al. |
| 5,001,091 A | 3/1991 | Pujari et al. ................ 501/103 |
| 5,421,864 A | 6/1995 | Chiba et al. |
| 5,665,511 A | 9/1997 | Imai et al. |
| 5,681,883 A | 10/1997 | Hill et al. |
| 6,160,042 A | 12/2000 | Ishida |
| 6,162,849 A | 12/2000 | Zhuo et al. |
| 6,645,612 B2 | 11/2003 | Pujari et al. |
| 6,652,822 B2 | 11/2003 | Phillips et al. |
| 6,913,827 B2 | 7/2005 | George et al. |
| 2003/0038278 A1* | 2/2003 | Ishihara ................ 252/500 |
| 2004/0007764 A1 | 1/2004 | Jang |
| 2004/0220419 A1 | 11/2004 | Gottschalk-Gaudig et al. |
| 2005/0041373 A1 | 2/2005 | Pruss et al. |
| 2005/0153124 A1 | 7/2005 | Finn et al. |
| 2006/0127422 A1* | 6/2006 | Lodyga et al. ............... 424/400 |

FOREIGN PATENT DOCUMENTS

| EP | 0198374 A | 10/1986 |
|---|---|---|
| EP | 424094 A | 4/1991 |
| JP | 05-051557 | 3/1993 |
| JP | 1993051540 | 3/1993 |
| JP | 07-215705 | 8/1995 |

OTHER PUBLICATIONS

Article: Neoalkoxy Titanate and Zirconate Coupling Agent Additives in Thermoplastics by Salvatore J. Monte. from Polymers & Polymer Composites, vol. 10, No. 2, 2002.

\* cited by examiner

*Primary Examiner*—Johann Richter
*Assistant Examiner*—Konata M. George
(74) *Attorney, Agent, or Firm*—Dominick G. Vicari

(57) ABSTRACT

A boron nitride composition having its surface treated with a coating layer comprising a zirconate coupling agent. The boron nitride composition can be used as fillers in polymeric compounds at levels of up to 90 wt. %, giving thermal conductivity of up to 35 W/mK.

34 Claims, 1 Drawing Sheet

ENHANCED BORON NITRIDE COMPOSITION AND POLYMER-BASED COMPOSITIONS MADE THEREWITH

CROSS-REFERENCE TO RELATED APPLICATIONS

This application claims the benefits of U.S. Provisional Patent Application No. 60/661,395. which was filed Mar. 14, 2005 and U.S. patent application Ser. No. 11/207,865 filed Aug. 19, 2005, which patent applications are fully incorporated herein by reference.

FIELD OF THE INVENTION

The present invention relates to a boron nitride composition, for use in applications including forming polymer-based compounds containing the boron nitride.

BACKGROUND OF THE INVENTION

Boron nitride ("BN") comes in a variety of crystalline structures and has a variety of uses from polishing agents to lubricants. Hexagonal boron nitride ("hBN") is a very desirable form and a white composition having hexagonal layer structure similar to graphite. Because of its properties, it has found uses in heat conductivity applications, electrical insulation applications, corrosion resistance applications, lubrication applications, and as a plastic additive. Boron nitride can be molded and used in composite materials or as a raw material for cubic boron nitride. It is used in many applications including electronic materials, non-oxidizing ceramics sintering filler powder, makeup materials, medical additives, etc.

In the prior art, BN may be manufactured in a high temperature reaction between inorganic raw materials into a white powder composition of BN particles, having a hexagonal structure similar to graphite in platelet morphology. When platelet BN is added as a filler to a polymer, a blended material is formed having poor rheological properties. At loaded concentrations above 30 wt. % BN, the blended material is so viscous that it is difficult to dispense from a mechanical dispenser such as a syringe.

U.S. Pat. No. 6,731,088 discloses a process to manufacture BN, forming a dry powder of spherically shaped agglomerates of irregular non-spherical particles bound together by a binder and subsequently spray-dried. The spherically shaped BN agglomerates can be compounded into polymer compositions at levels of 35-50 wt. % for compositions with viscosity below about 300 cp.

JP Publication No. 05-051540 discloses BN powder treated with at least a titanate coupling agent, a silane coupling agent, and a non-inonic coupling agent in an amount of 0.1 to 5 wt. %, to improve the wettability of the BN in applications such as a release agent, a lubricant, a low-friction material, a coating material, etc. U.S. Pat. No. 6,162,849 discloses a thermally conductive moldable polymer blend having at least 60 wt. % of BN powder having an average particle size of at least 60 microns and coated with a coupling agent, and wherein the thermally conductive composition has a thermal conductivity of at least 15 W/m ° K.

There is still a need for improved BN compositions, particularly for BN compositions that can be used in large quantities as a filler in applications such as electronic materials, thermally conductive compositions, and the like. Applicants have found the surface functionalization of BN with a zirconate coupling agent helps reduce the viscosity of the polymeric compound, allowing more BN filler to be added and thus improving the overall thermal conductivity of the material.

BRIEF SUMMARY OF THE INVENTION

A boron nitride powder having deposited on the surface thereof a coating layer comprising 0.5 to 5 wt. % of at least one of a zirconate coupling agent, a zirconium aluminate coupling agent, an aluminate coupling agent, and mixtures thereof. In one embodiment, the boron nitride powder comprises spherically shaped agglomerates of irregular non-spherical BN particles bound together by a binder and subsequently spray-dried.

The invention further relates to a polymeric composition comprising at least 35 wt. % of a boron nitride powder coated with 0.5 to 5 wt. % of a zirconate coupling agent.

Lastly, the invention relates to a method for increasing the thermal conductivity of polymeric compositions, said method comprises mixing in the composition at least 35 wt. % of a boron nitride powder having deposited on the surface thereof a coating layer comprising at least one of a zirconate coupling agent, a zirconium aluminate coupling agent, an aluminate coupling agent, or mixtures thereof.

DETAILED DESCRIPTION OF THE INVENTION

Figure 1:
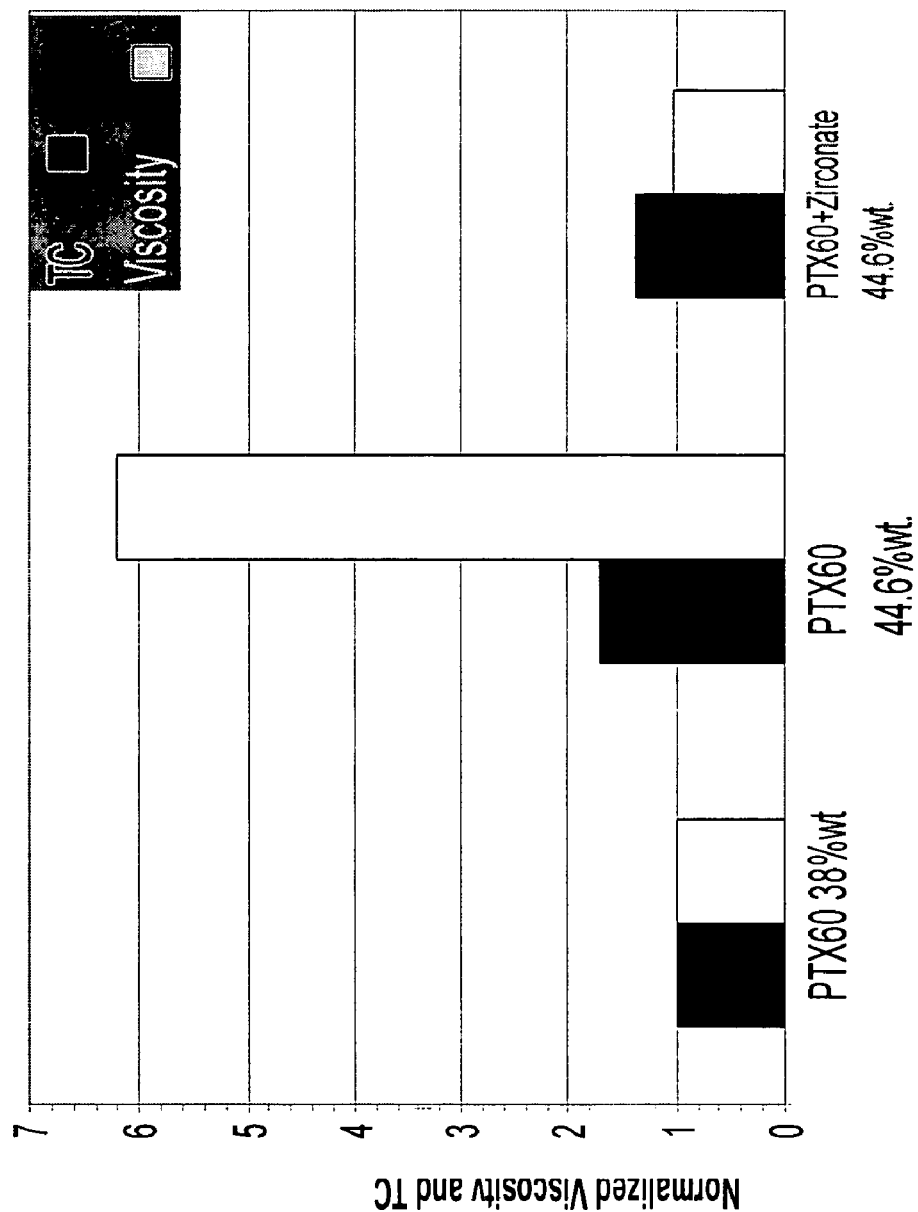
FIG. 1 is a graph showing the changes in viscosity and thermal conductivity (TC) in compositions with untreated BN and BN functionalized with a zirconate coupling agent.

As used herein, approximating language may be applied to modify any quantitative representation that may vary without resulting in a change in the basic function to which it is related. Accordingly, a value modified by a term or terms, such as "about" and "substantially," may not to be limited to the precise value specified, in some cases.

As used herein, the term "functionalized" may be used interchangeably with "surface functionalized," "functionalized surface," "coated," "surface treated," or "treated," referring to the coating of the boron nitride component in agglomerate form or platelet form with the coupling agent of the invention.

As used herein, the term "functionalization" or "functionalized" relates to modification of the BN surface to provide a plurality of functional groups on the BN surface. A "functionalized surface" as used herein refers to the coating that has been modified so that a plurality of functional groups are covalently attached thereto, either directly or indirectly.

As used herein, the phrase "effective amount" or "sufficient amount" means that amount sufficient to bring about the desired effect, e.g., lowering the viscosity of a polymeric composition at least 20% over the viscosity of a polymeric composition not having this effective amount.

Boron Nitride Component. As the starting material, the BN component comprises crystalline or partially crystalline boron nitride particles made by processes known in the art. These include spherical BN particles in the micron size range produced in a process utilizing a plasma gas as disclosed in U.S. Pat. No. 6,652,822; hBN powder comprising spherical boron nitride agglomerates are formed of irregular non-spherical BN particles bound together by a binder and subsequently spray-dried, as disclosed in US Patent Publication No. US2001/0021740; BN powder produced from a pressing process as disclosed in U.S. Pat. Nos. 5,898,009 and 6,048,511; BN agglomerated powder as disclosed in US Patent Publication No. 2005.0041373; BN powder having high thermal diffusivity as disclosed in US Patent Publication No. US20040208812A1; and highly delaminated BN powder as disclosed in U.S. Pat. No. 6,951,583.

In one embodiment, the BN powder has an average particle size of at least 50 microns. In another embodiment, the BN powder has an average particle size of 5 to 500 microns. In a third embodiment, from 10 to 100 microns.

In one embodiment, the BN powder comprises irregularly shaped agglomerates of hBN platelets, having an average particle size of above 10 microns.

In another embodiment, the BN powder is in the form of spherical agglomerates of hBN platelets. In one embodiment of spherical BN powder, the agglomerates have an average agglomerate size distribution (ASD) or diameter from 10 to 500 microns. In another embodiment, the BN powder is in the form of spherical agglomerates having an ASD in the range of 30 to 125 microns. In one embodiment, the ASD is 74 to 100 microns. In another embodiment, 10 to 40 microns.

In one embodiment, the BN powder is in the form of platelets having an average diameter of at least about 1 micron, and typically between about 1 and 20 μm, and a thickness of no more than about 50. In another embodiment, the powder is in the form of platelets having an average aspect ratio of from about 50 to about 300.

In one embodiment, the BN is an h-BN powder having a highly ordered hexagonal structure with a crystallization index of at least 0.12. In another embodiment, the BN powder has a crystallinity of about 0.20 to about 0.55, and in yet another embodiment, from about 0.30 to about 0.55.

In applications wherein the BN powder is to be used as fillers in polymer composites, e.g., microprocessor packaging requiring high thermal conductivity properties, 10 to 40 vol. % of the BN powder display an average particle size of about 5 to 25 microns; about 60 to 90 vol. % of the particles display an average particle size of about 40 to 80 microns.

In one embodiment and prior to being functionalized or mixed into a polymer composite, the BN powder is dried in a forced air oven for about 300° F. for at least 6 hrs. and then kept at 120° F. before being treated or before mixing.

In one embodiment and prior to being functionalized or mixed into a polymer composite, the BN is sintered at a temperature of at least 1800° C. for about 1 to 4 hrs. Suitable atmospheres for sintering include inert gas, nitrogen, and argon. In one embodiment, the sintering is in a vacuum.

In another embodiment, the hBN particles are first washed in 2% glacial acetic acid de-ionized water solution to remove possible residual surface contaminants from powder processing, in an amount of 5-10 wt. % BN solid in water solution. The solution is stirred at 80-100° C. for a few hours then vacuum filtered. The BN particles may then be washed again with fresh deionized water before being dried in air circulating oven at 110° C. prior to the next step of being functionalized/coated with the coupling agent.

Organometallic Coupling Agent. The BN powder of the invention is functionalized or coated in one invention with about 0.5 to about 10 wt. % of an organometallic coupling agent. In another embodiment, the BN is coated with about 1 to about 5 wt. % of an organometallic coupling agent.

In one embodiment, the coupling agent comprises a zirconate-containing compound. Examples include ethylenecally unsaturated zirconate containing compound, neoalkoxy zirconate containing compound, neoalkoxytrisneodecanoyl zirconate, neoalkoxytris(dodecyl)benzenesulfonyl zirconate, neoalkoxytris(dioctyl)phosphate zirconate, neoalkoxytris (dioctyl)pyrophosphate zirconate, neoalkoxytris (ethylenediamino)ethyl zirconate, neoalkoxytris(m-amino)phenyl zirconate, tetra (2,2 diallyloxymethyl)butyl, di(ditridecyl) phosphito zirconate (commercially available as KZ 55 from Kenrich Petrochemicals, Inc. "Kenrich"), neopentyl(diallyl) oxy, trineodecanoyl zirconate (commercially available as NZ 01 from Kenrich), neopentyl(diallyl)oxy, tri(dodecyl)benzene-sulfony zirconate (commercially available as NZ 09 from Kenrich), neopentyl(diallyl)oxy, tri(dioctyl)phosphato zirconate (commercially available as NZ 12 from Kenrich), neopentyl(diallyl)oxy, tri(dioctyl)pyro-phosphato zirconate (commercially available as NZ 38 from Kenrich), neopentyl (diallyl)oxy, tri(N-ethylenediamino)ethyl zirconate (commercially available as NZ 44 from Kenrich), neopentyl(diallyl)oxy, tri(m-amino)phenyl zirconate (commercially available as NZ 97 from Kenrich), neopentyl(diallyl)oxy, trimethacryl zirconate (commercially available as NZ 33 from Kenrich), neopentyl(diallyl)oxy, triacryl zirconate (formerly available as NZ 39 from Kenrich), dineopentyl(diallyl)oxy, diparamino benzoyl zirconate (commercially available as NZ 37 from Kenrich), dineopentyl(aiallyl)oxy, di(3-mercapto) propionic zirconate (commercially available as NZ 66A from Kenrich), zirconium IV 2,2-bis(2-propenolatomethyl) butanolato, cyclo di[2,2-(bis 2-propenolatomethyl) butanolato]Pyrophosphato —O,O (commercially available as Ken-React® KZ TPP® from Kenrich), and mixtures thereof.

In one embodiment, the zirconate-coupling, agent is an organo functional alkoxide of zirconium, and wherein the alkoxide is compatible and active in water. By active, it is meant that the zirconate is not fully reacted or do not have too rapid a rate of reaction with water to produce substantial amounts of zirconium dioxide. Examples include neoalkoxytrisneodecanoyl zirconate, neoalkoxytris(dodecyl) benzenesulfonyl zirconate, neoalkoxytris(dioctyl) phosphate zirconate, neoalkoxytris(dioctyl) pyrophosphate zirconate, neoalkoxytris(ethylenediamino) ethyl zirconate, neoalkoxytris (m-amino)phenyl zirconate, and the like as disclosed in Japanese Patent Application No. 64-52786, Japanese Patent Application No. 01-108277, and Japanese Application No. 01-129031.

In one embodiment, the coupling agent comprises a coupling agent system of aluminum such as a zirconium aluminate-coupling agent, or an aluminate-coupling agent as disclosed in EP Patent Publication No. 198374. Examples of aluminate coupling agents include diisobutyl(oleyl)aceto acetyl aluminate or alkylacetoacetate aluminum di-isopropylate, commercially available from Ajinomoto.

Optional Additives: In one embodiment, additives including initiators, dispersants, defoaming agents, and adhesion promoters may be optionally added to the coupling agent. Initiator examples include thermal initiators, chemical initiators, electron beam initiators, and photoinitiators.

Method for Preparing the BN Composition There are various methods for preparing the BN composition of the invention, including a dry method and a wet method.

An example of a dry method is mixing, wherein the zirconate coupling agent is mixed directly with the BN to be treated using a mixer or the like. Other dry methods including tumbling, prilling (also known as perforated pan coating), among others.

In the wet method, the zirconate coupling agent, the BN powder, and optional materials are treated in a solvent and the solvent is subsequently removed. The solvent can be organic solvents and water. Other wet methods include spray coating and washing.

Examples of organic solvents include aromatic solvents such as toluene, xylene, and the like; hydrocarbon solvents such as hexane, octane, and the like; esters such as ethyl acetate, butyl acetate, and the like; and ethers such as ethyl ether and the like. In one embodiment, the solvent is used in an amount of 30-3000 parts by weight based on 100 parts by weight of the zirconate-coupling agent.

In an embodiment of a wet method wherein the solvent is water, the BN particles are treated with 100 parts by weight of a zirconate base coupling agent having unhydrolyzable side chains with a solubility parameter (x) of 6.5-12; 3 to 30 parts by weight of a nonionic surface active agent blended therewith having an HLB value (y) of 2-30 and containing no protonic hydrogen(s) in its molecule, wherein x and y satisfy a relationship of 4x−24<=y<=4x−18.

In a second embodiment of a wet method using water as a solvent, the BN particles are treated with a mixture of a cyclo[dineopentyl(diallyl)]pyrophosphate dineopentyl(diallyl) zirconate and a surfactant such as sodium dodecylbenzene-sulfonate, ethoxylated nonyl phenol or cetyl trimethyl ammonium chloride.

Preparing Polymeric Compound Containing BN Surface Functionalized with Zirconate: The BN composition prepared in any of the methods above may be used in the powder form, or incorporate into a paste form of about 60 to 80 wt. % of solid BN in an aqueous or non-aqueous medium of IPA, methanol, ethanol and the like. In polymeric compounds, the BN in powder or paste form is used in amounts of 30 to 80 wt. % of BN to total weight of the compounds, along with a polymeric matrix component such as a polyester, a melt-processable polymer, a phenolic, a silicone polymer (e.g., a silicone rubber), an acrylic, a wax, a thermoplastic polymer, a low molecular weight fluid, or an epoxy molding compound, for a thermal conductivity of about 1 W/mK to about 25 W/mK. In one embodiment, the zirconate surface treated BN is used as a filler in levels of up to 90% for increasing thermal conductivity of up to 37.5 W/mK or higher.

In one embodiment, the thermoplastic polymer matrix comprises at least one of a liquid crystal polymer; a polyester such as polyethylene naphthalate, polyethylene terephthalate, polybutylene terephthalate; a polyamide; a polyphthalamide; a polyimide; a polyphenylene sulfide; a polycarbonates; a polyetheretherketone; apolyaryletherketone; a polyphenylene oxide; and a mixture thereof.

The polymeric compound containing zirconate coated BN may be prepared by techniques known in the art, such as melt-mixing in equipment such as a mill, a Banbury, a Brabender, a single or twin screw extruder, continuous mixers, kneaders, etc.

In one embodiment, the polymer, the untreated BN powder, and the zirconate coupling agent may all be intimately mixed in the form of granules and/or powder in a high shear mixer. In yet another embodiment, the zirconate-coupling agent may be first added to the polymer matrix, the BN filler is subsequently added to the mixture for an intimate mixing process in which the BN particles are surface treated with the zirconate-coupling agent.

The surface-treated BN of the invention allows the loading concentration of BN to be raised with little increases in the viscosity of the composite, relative to the same composite loaded with untreated BN; thereby providing enhanced thermal conductivity and lower viscosity or simply to reduce the viscosity of the filled polymer composite to enhance its processability. In one embodiment, the surface-treated BN composition when blended into a polymer composite, lowers the viscosity of the polymeric composite at least 20% over the viscosity of the polymeric composition containing the same amount of boron nitride powder not treated with the zirconate-coupling agent. In another embodiment, the viscosity is lowered at least 50%, particularly when the surface-treated BN is added in an amount of greater than 20 wt. % (based on the total weight of the polymer composite with BN filler)

Polymer composites comprising the BN powder functionalized with the zirconate coupling agent of the invention may be used for a number of applications, including microprocessor packaging, bearing housings, heat-exchanger applications such as heat sinks for microprocessors and integrated circuit chips, plastic ball grid array packages, quad flat packs, and other common surface-mounted integrated circuit packages, etc., particularly applications demanding a high thermal conductivity which is close to that of pure alumina (about 25 W/m°K).

Examples are provided herein to illustrate the invention but are not intended to limit the scope of the invention.

In all examples, Ken-React® KZ TPP® Zirconate, or Zirconium IV 2,2-bis(2-propenolatomethyl) butanolato, cyclo di [2,2-(bis 2-propenolatomethyl) butanolato]pyrophosphato —O,O, from Kenrich is used as the coupling agent.

BN powder is commercially available from GE Advanced Ceramics located in Cleveland, Ohio, as PTX60 (spherical agglomerates of hexagonal platelet BN with an average particle size of 60 microns); PT120 (hexagonal platelet BN having an average particle size of 12 microns); and PT110 (hexagonal platelet BN having an average particle size of 45 microns).

EXAMPLE 1

In this example, 1 part of Ken-React® KZ TPP® zirconate coupling agent from Kenrich is dissolved in 1000 parts of toluene, then 100 parts PT120 (BN powder having ave. particle sizes of 12μ) is added to the mixture. The mixture is agitated for about 10 minutes, then the toluene solvent is removed by suction filtration.

EXAMPLE 2

PT110 BN powder is added to a high speed churning machine such as a Henschel mixer, then Ken-React® KZ TPP® zirconate coupling agent is slowly added to the mixer while churning continues for uniform mixing/coating of the BN particles. The surface functionalized BN is subsequently used as filler in lubricant materials or thermally conductive composites.

EXAMPLES 3-5

Viscosity Measurements

PTX60 BN powder is first coated with 1.44 wt. % Ken-React® KZ TPP® zirconate via V-blending for about 15 to 60 minutes. The blended powder is then mixed with silicone fluid (Dow Corning 200 fluid-100 CST) using a FlackTek speed mixer for about 20 seconds at approximately 3500 rpm. The viscosity, in poise, is measured using Advanced Rheometer 2000 (TA Instruments). The results using various surface treated BN levels are shown in Table 1.

TABLE 1

| Example | Treated BN loading (wt. %) | Ave. Viscosity (poise, 1 s$^{-1}$) |
|---|---|---|
| 3 | 35 | 58 |
| 4 | 40 | 341 |
| 5 | 45 | 1202 |

EXAMPLES 6-7

In the examples, polymer composites comprising treated and untreated BN fillers are prepared and measured for thermal conductivity. In the examples, treated BN powder is prepared by first mixing the powder with Ken-React® KZ TPP® zirconate via V-blending for about 15 to 60 minutes. The treated BN powder is then mixed with 27 wt. % Sylgard 184 Silicone Resin and 3 wt. % curing agent Sylgard 184 in a FlackTek speed mixer at approximately 3500 rpm. The mixture is placed in a 3"×6" rectangular mold and pressed at 125° C. for 45 minutes to form pads of 0.5 to 1.5 mm in thickness. The bulk thermal conductivity in W/mK is measured via a Hot Disk® Thermal Constants Analyzer. The results are shown in Table 2:

TABLE 2

| Example | Composition | Thermal Conductivity |
| --- | --- | --- |
| 6 | 30% Silicone Resin + 70% untreated BN (64% PT110 and 6% PT120) | 11.53 W/mK |
| 7 | 30% Silicone Resin + 70% Zirconate treated BN (64% PT110 with 2.15% Zirconate and 6% PT120 with 2.3% Zirconate) | 10.47 W/mK |

EXAMPLES 8-24

BN Coated with Different Levels of Zirconate and at Different Loadings

In the examples as shown in Table 3, PTX60 BN powder is v-blended with Ken-React® KZ TPP® zirconate and then mixed with silicone fluid (Dow Corning 200 fluid-100 CST) using a FlackTek speed mixer for about 20 seconds at approximately 3500. The viscosity, in poise, is measured using Advanced Rheometer 2000 (TA Instruments). The BN coated is also mixed in a FlackTek speed mixer at approximately 3500 rpm with 35-60 wt. % of Sylgard 184 Silicone Resin and 3.5 to 6.0 wt. % curing agent Sylgard 184, both from Dow Corning. The filler content of spherical BN ranges from 35 to 59 wt. % (20 to 40 vol. %). The mixture is placed in a 3"×6" rectangular mold and pressed at 125° C. for 45 minutes to form pads of 0.5 to 1.5 mm in thickness. The bulk thermal conductivity is measured via a Hot Disk® Thermal Constants Analyzer.

For samples containing untreated BN powder, the BN (PTX60) is V-blended by itself just for comparison.

TABLE 3

| Example | Treated BN loading (wt. %) | Wt. % zirconate in BN | Ave. Viscosity (poise, 1 s$^{-1}$) | Thermal Conductivity (W/mK) |
| --- | --- | --- | --- | --- |
| 8 | 35 | 0.0 | 103 | 1.80 |
| 9 | 35 | 1.4 | 58 | 1.64 |
| 10 | 35 | 2.5 | 45 | 1.63 |
| 11 | 35 | 3.5 | 46 | 1.62 |
| 12 | 40 | 0.0 | 494 | 2.47 |
| 13 | 40 | 1.4 | 341 | 2.27 |
| 14 | 40 | 2.5 | 238 | 1.97 |
| 15 | 40 | 3.5 | 275 | 2.16 |
| 16 | 45 | 0.0 | 3079 | 3.55 |
| 17 | 45 | 1.4 | 1202 | 3.49 |
| 18 | 45 | 2.5 | 708 | 3.26 |
| 19 | 45 | 3.5 | 769 | 3.27 |
| 20 | 50 | 0.0 | 37716 | 5.20 |
| 21 | 50 | 1.4 | 6020 | 5.06 |
| 22 | 50 | 2.5 | 2784 | 4.81 |
| 23 | 50 | 3.5 | 3661 | 4.59 |
| 24 | 60 | 2.1 | — | 8.86 |

Table 4 illustrates the properties of some of zirconate coated BN powder in the examples above. Oxygen %, soluble borates, and carbon content increase with addition of zirconates. The average particle size (D50) is shown as well as the D10 and D90 correspond to the 10% and 90% percentile of the distribution, respectively.

TABLE 4

| | PTX60 BN | PTX60 + 1.4% Zirconate TPP | PTX60 + 2.5% Zirconate TPP | PTX60 + 3% Zirconate TPP |
| --- | --- | --- | --- | --- |
| Oxygen (%) | 0.1017 | 1.009 | 1.528 | 2.259 |
| Carbon (%) | 0.01561 | 0.982 | 1.82 | 2.22 |
| SA (m2/g) | 5.92 | | | |
| Sol. Borate (%) | 0.03 | 0.09 | 0.05 | 0.05 |
| D10 (microns) | 17.1 | 9.805 | 11.71 | 16.29 |
| D50 (microns) | 55.77 | 38.28 | 41.88 | 48.15 |
| D90 (microns) | 87.23 | 77.39 | 78.39 | 82.13 |

EXAMPLES 25-28

The samples are prepared in the same manner as in Examples 10-26 and the results are shown in Table 5 and also as illustrated in FIG. 1. These demonstrate that surface functionalization of BN with a zirconate coupling agent help reduce the viscosity of the polymeric compound, allowing more BN filler to be added and thus improving the overall thermal conductivity of the material. In examples 27 and 29, the untreated BN powder PTX60 is not V-blended and used as received.

TABLE 5

| Example | Treated BN loading (wt. %) | Wt. % zirconate in BN | Ave. Viscosity (poise, 1 s$^{-1}$) | Thermal Conductivity (W/mK) |
| --- | --- | --- | --- | --- |
| 25 | 38 | 0.0 | 755 | 2.33 |
| 26 | 38 | 2.5 | 114 | 1.86 |
| 27 | 44.6 | 0 | 4652 | 3.96 |
| 28 | 44.6 | 2.5 | 755 | 3.22 |

COMPARATIVE EXAMPLES

In the comparative examples with polymeric resins as a coating/functionalization agent, spherical BN PTX60 is V-blended with 0-15 wt. % silicone fluid (Dow Corning 200 fluid-5 CST), and further mixed with silicone fluid (Dow Corning 200 fluid-100 CST) using a FlackTek speed mixer for about 20 seconds and at approximately 3500. The viscosity, in poise, is measured using Advanced Rheometer 2000 (TA Instruments).

For thermal conductivity measurements, spherical BN PTX60 coated with silicone fluid at various levels (35 to 59 wt. % or 20 to 40 vol. %) is mixed in a FlackTek speed mixer at approximately 3500 rpm with 35-60 wt. % of Sylgard 184 Silicone Resin and 3.5 to 6.0 wt. % curing agent Sylgard 184. The mixture is placed in a 3"×6" rectangular mold and pressed at 125° C. for 45 minutes to form pads of 0.5 to 1.5 mm in thickness.

As illustrated in Table 6, the use of spherical BN coated with silicone fluid in polymeric compositions helps reduce viscosity and increase the loading. However, the thermal conductivity data is not as good as with spherical BN coated with ziroconate.

TABLE 6

| Example | wt. % loading of BN treated with silicone | Wt. % silicone fluid (5 CST) in BN | Ave. Viscosity | Thermal Conductivity |
|---|---|---|---|---|
| 29 | 39 | 0.0 | 1220 | 2.64 |
| 30 | 39 | 5.0 | 1033 | — |
| 31 | 39 | 10.0 | 355 | — |
| 32 | 39 | 15.00 | 122 | — |
| 33 | 42 | 5.00 | 1220 | 2.52 |
| 34 | 44.5 | 10.0 | 1220 | 2.50 |
| 35 | 48 | 15.00 | 1220 | 2.46 |

It should be noted that the zirconate coupling agent of the invention may be used to functionalize other ceramic fillers besides boron nitride, including the typical ceramic fillers used for thermal interface management (TIM) applications such as aluminum nitride, aluminum oxide, and the like.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

All citations referred herein are expressly incorporated herein by reference.

The invention claimed is:

1. A boron nitride composition comprising boron nitride powder, the boron nitride powder having its surface treated with a coating layer, wherein the coating layer comprises about 0.5 to about 10 wt. % of at least one of a zirconate coupling agent, a zirconium aluminate coupling agent, and mixtures thereof.

2. The boron nitride composition of claim 1, wherein the coating layer comprising about 1 to about 5 wt. % of a zirconate coupling agent.

3. The boron nitride composition of claim 1, wherein the zirconate coupling agent is selected from the group of an ethyleneically unsaturated zirconate containing compound, a neoalkoxy zirconate containing compound, and mixtures thereof.

4. The boron nitride composition of claim 1, wherein the zirconate coupling agent is an organo functional alkoxide of zirconium, and wherein the alkoxide is compatible and active in water.

5. The boron nitride composition of claim 1, wherein the boron nitride powder has an average particle size of at least 50 microns.

6. The boron nitride composition of claim 1, wherein the boron nitride powder comprises spherically shaped agglomerates of irregular non-spherical particles bound together by a binder and subsequently spray-dried.

7. The boron nitride composition of claim 1, wherein the boron nitride powder comprises hexagonal boron nitride platelets having an aspect ratio of from about 50 to about 300.

8. The boron nitride composition of claim 1, wherein the boron nitride powder comprises hexagonal boron nitride platelets having an average diameter of from about 2 :m to about 20 :m.

9. The boron nitride composition of claim 1, wherein the boron nitride powder comprises irregularly shaped agglomerates of hexagonal boron nitride platelets, having an average particle size of above 10 microns.

10. A polymer composite comprising a polymer matrix selected from the group of a thermoplastic resin, an epoxy resin, a silicone resin, and a filler material comprising particles of boron nitride treated with a coating layer comprising 0.5 to 10 wt. % of at least one of a zirconate coupling agent, a zirconium aluminate coupling agent, and mixtures thereof.

11. The polymer composite of claim 10, wherein the polymer matrix comprises a silicone resin.

12. The polymer composite of claim 10, wherein the polymer matrix comprises at least one of a liquid crystal polymer; polyethylene naphthalate, polyethylene terephthalate, polybutylene terephthalate; a polyamide; a polyimide; a polyphthalamide; a polyphenylene sulfide; a polycarbonate; a polyetheretherketone; apolyaryletherketone; a polyphenylene oxide; and a mixture thereof.

13. A polymer composite comprising a polymer matrix selected from the group of a thermoplastic resin, an epoxy resin, a silicone resin, and a filler material comprising particles of boron nitride, wherein the boron nitride is treated with a coating layer comprising about 1 to about 5 wt. % of a zirconate coupling agent.

14. The polymer composite of claim 13, wherein the zirconate coupling agent is selected from the group of an ethyleneically unsaturated zirconate containing compound, a neoalkoxy zirconate containing compound, and mixtures thereof.

15. An article comprising the boron nitride composition of claim 1.

16. A method for producing boron nitride powder for forming polymer composites having reduced viscosity, said process comprises the step of coating the boron nitride powder with a composition comprising a zirconate coupling agent for a sufficient amount of time for the boron nitride powder to be coated with a sufficient amount of the zirconate coupling agent.

17. The method of claim 16, wherein the boron nitride is coated with the zirconate coupling agent by at least one of tumbling, prilling, or spray coating.

18. The method of claim 16, wherein the zirconate coupling agent is an organo functional alkoxide of zirconium, and wherein the alkoxide is compatible and active in water.

19. The boron nitride composition of claim 1, wherein said composition when blended into a polymeric composition, lowers the viscosity of the polymeric composition at least 20% over the viscosity of the polymeric composition containing the same amount of boron nitride powder not treated with the zirconate coupling agent.

20. The boron nitride composition of claim 1 wherein the coupling agent is a zirconate selected from the group consisting of neoalkoxytrisneodecanoyl zirconate, neoalkoxytris (dodecyl)benzenesulfonyl zirconate, neoalkoxytris(dioctyl) phosphate zirconate, neoalkoxytris(dioctyl)pyrophosphate zirconate, neoalkoxytris (ethylenediamino)ethyl zirconate, neoalkoxytris(m-amino)phenyl zirconate, tetra(2,2 diallyloxymethyl)butyl, di(ditridecyl)phosphito zirconate, neopentyl(diallyl)oxy trineodecanoyl zirconate, neopentyl(diallyl) oxy tri(dodecyl)benzene-sulfonyl zirconate, neopentyl (diallyl)oxy tri(dioctyl)phosphato zirconate, neopentyl (diallyl)oxy tri(dioctyl)pyro-phosphato zirconate, neopentyl (diallyl)oxy tri(N-ethylenediamino)ethyl zirconate, neopentyl(diallyl)oxy tri(m-amino)phenyl zirconate, neopentyl(diallyl)oxy trimethacryl zirconate, neopentyl(diallyl) oxy triacryl zirconate, dineopentyl(diallyl)oxy diparamino benzoyl zirconate, dineopentyl(aiallyl)oxy di(3-mercapto) propionic zirconate, zirconium IV 2,2-bis(2-propenolatomethyl) butanolato cyclo di [2,2-(bis 2-propenolatomethyl) butanolato]pyrophosphato-O,O, neoalkoxytrisneodecanoyl zirconate, neoalkoxytris(dodecyl) benzenesulfonyl zirconate, neoalkoxytris(dioctyl) phosphate zirconate, neoalkoxytris(dioctyl) pyrophosphate zirconate, neoalkoxytris(ethylenediamino) ethyl zirconate, neoalkoxytris (m-amino)phenyl zirconate and combinations thereof.

21. The boron nitride composition of claim 1 wherein the coupling agent further includes one or more additives selected from the group consisting of thermal initiators, chemical initiators, electron beam initiators, photoinitiators, dispersants, defoaming agents and adhesion promoters.

22. The method of claim 16 wherein the boron nitride and coupling agent are combined in an aqueous or organic solvent, wherein the solvent is subsequently removed.

23. The method of claim 22 wherein the solvent is an organic liquid selected from the group consisting of toluene, xylene, hexane, octane, ethyl acetate, butyl acetate and ethyl ether.

24. A boron nitride composition comprising boron nitride powder, the boron nitride powder having its surface treated with a coating layer comprising at least one of a zirconate coupling agent, a zirconium aluminate coupling agent, an organo-aluminate coupling agent selected from the group consisting of diisobutyl (oleyl) aceto acetyl aluminate and alkylacetoacetate aluminum diisopropylate, and mixtures thereof.

25. The boron nitride composition of claim 24, wherein the boron nitride powder has an average particle size of at least 50 microns.

26. The boron nitride composition of claim 24, wherein the boron nitride powder comprises spherically shaped agglomerates of irregular non-spherical particles bound together by a binder and subsequently spray-dried.

27. The boron nitride composition of claim 24, wherein the boron nitride powder comprises hexagonal boron nitride platelets having an aspect ratio of from about 50 to about 300.

28. The boron nitride composition of claim 24, wherein the boron nitride powder comprises hexagonal boron nitride platelets having an average diameter of from about 2 :m to about 20 :m.

29. The boron nitride composition of claim 24, wherein the boron nitride powder comprises irregularly shaped agglomerates of hexagonal boron nitride platelets, having an average particle size of above 10 microns.

30. A polymer composite comprising a polymer matrix selected from the group of a thermoplastic resin, an epoxy resin, a silicone resin, and a filler material comprising particles of boron nitride treated with a coating layer comprising 0.5 to 10 wt. % of at least one of a zirconate coupling agent, a zirconium aluminate coupling agent, an organo-aluminate coupling agent selected from the group consisting of diisobutyl(oleyl)aceto acetyl aluminate and alkylacetoacetate aluminum diisopropylate, and mixtures thereof.

31. The polymer composite of claim 30, wherein the polymer matrix comprises a silicone resin.

32. The polymer composite of claim 30, wherein the polymer matrix comprises at least one of a liquid crystal polymer; polyethylene naphthalate, polyethylene terephthalate, polybutylene terephthalate; a polyamide; a polyimide; a polyphthalamide; a polyphenylene sulfide; a polycarbonate; a potyetheretherketone; a polyaryletherketone; a polyphenylene oxide; and a mixture thereof.

33. The polymer composite of claim 30, wherein the boron nitride is treated with a coating layer comprising about 1 to about 5 wt. % of the zirconate coupling agent.

34. The polymer composite of claim 33, wherein the zirconate coupling agent is selected from the group of an ethyleneically unsaturated zirconate containing compound, a neoalkoxy zirconate containing compound, and mixtures thereof.

* * * * *